US008088731B2

(12) United States Patent
Knudsen et al.

(10) Patent No.: US 8,088,731 B2
(45) Date of Patent: Jan. 3, 2012

(54) USE OF GLP-1 COMPOUND FOR TREATMENT OF CRITICALLY ILL PATIENTS

(75) Inventors: Lotte Bjerre Knudsen, Valby (DK); Johan Selmer, Farum (DK); Kristian Tage Hansen, Slangerup (DK)

(73) Assignee: Novo Nordisk A/S, Bagsvaerd (DK)

( * ) Notice: Subject to any disclaimer, the term of this patent is extended or adjusted under 35 U.S.C. 154(b) by 39 days.

(21) Appl. No.: 12/496,910

(22) Filed: Jul. 2, 2009

(65) Prior Publication Data
US 2010/0311651 A1 Dec. 9, 2010

Related U.S. Application Data

(63) Continuation of application No. 11/451,635, filed on Jun. 13, 2006, now abandoned, which is a continuation of application No. 10/359,324, filed on Feb. 6, 2003, now abandoned.

(60) Provisional application No. 60/359,834, filed on Feb. 26, 2002.

(30) Foreign Application Priority Data

Feb. 7, 2002 (DK) .................................. 2002 00184

(51) Int. Cl.
*A61K 38/26* (2006.01)
*A61P 3/10* (2006.01)
*A61P 7/12* (2006.01)
*C07K 14/605* (2006.01)

(52) U.S. Cl. ........................................................ 514/7.2
(58) Field of Classification Search ........................ None
See application file for complete search history.

(56) References Cited

U.S. PATENT DOCUMENTS

| 5,000,953 | A | 3/1991 | Ui et al. |
| 5,155,031 | A | 10/1992 | Posner et al. |
| 5,614,492 | A | 3/1997 | Habener |
| 5,691,386 | A | 11/1997 | Inman et al. |
| 5,821,217 | A | 10/1998 | Forse et al. |
| 5,861,266 | A | 1/1999 | Ullrich et al. |
| 6,006,753 | A | 12/1999 | Efendic |
| 6,277,819 | B1 | 8/2001 | Efendic |
| 6,335,316 | B1 | 1/2002 | Hughes et al. |
| RE37,971 | E | 1/2003 | Baker et al. |
| 6,551,992 | B1 | 4/2003 | DeFelippis et al. |
| 6,703,359 | B1 | 3/2004 | Young et al. |
| 6,969,702 | B2 | 11/2005 | Bertilsson et al. |
| 7,491,187 | B2 * | 2/2009 | Van Den Berghe et al. .... 604/66 |
| 2002/0107178 | A1 | 8/2002 | Van Den Berghe |
| 2003/0199445 | A1 | 10/2003 | Knudsen et al. |

FOREIGN PATENT DOCUMENTS

| RU | 2036659 | 6/1995 |
| WO | WO 95/23217 | 8/1995 |
| WO | WO 97/07814 | 3/1997 |
| WO | WO 98/08531 | 3/1998 |
| WO | WO 98/08873 | 3/1998 |
| WO | WO 00/16797 | 3/2000 |
| WO | WO 00/33839 | 6/2000 |
| WO | WO 01/85256 | 11/2001 |
| WO | WO 03/028626 | 4/2003 |

OTHER PUBLICATIONS

W.S. Messer, "Vasopressin and Oxytocin", web document updated Apr. 3, 2000; http://www.neurosci.pharm.utoledo.edu/MBC3320/vasopressin.htm; 5 pages.*
Abstract US 19925044940, Novo Blood Cir. Path. Inst. Derwent Accession No. 1996-096010[10].
K.O. Case et al., "Nutrition Support in the Critically Ill Patient", Crit. Care Nurs Q 12000,m vol. 22, No. 4, pp. 75-89 (2000).
Y. Sakuri et al., "Stimulation of Muscle Protein Synthesis By Long-Term Insulin Infusion in Severely Burned Patients", Annals of Surgery, vol. 222, No. 3, pp. 283-297 (1995).
Iapichino et al., L'usage de l'insulin comme agent anabolisant doit-il Etre preconise chez le subject denutri ou agresse, Nutr. Clin. Metabol., vol. 10, pp. 243-252 (translation included).
Critical Illness Polyneuropathy ; Brain ; Zochodne, Douglas W. et al. ; vol. 110, pp. 819-842 ; (1987).
Critical Illness Polyneuropathy ; Clinical Neurology and Neurosurgery ; Leijten, F.S.S. et al., vol. 96, p. 10-19 ; (1994).
Acute Weakness ; Oxford Textbook of Critical Care ; Bolton, C.F.; pp. 490-495; (1999).
Sepsis and the systemic inflammatory response syndrome; Critical Care Medicine; Bolton, Charles F., vol. 24, Part 8, pp. 1408-1416 (1996).
The American Journal of medicine, Mizock, Barry A., vol. 98, pp. 75-84 (1995).
K.C. McCowen et al., "Stress-Induced Hyperglycemia", Critical Care Clinics, vol. 17, No. 1, pp. 107-124 (2001).
Press Release "Clinical Study demonstrates impressive life-saving effects of insulin by tight control of glucose in intensive care patients", pp. 1-3 (Nov. 8, 2001).
UK Prospective Diabetes Study (UKPDS) Group "Intensive blood-glucose control with supphonylureas or insulin compared with conventional treatment and risk of complications in patients with type 2 diabetes", The Lancet, vol. 352, pp. 837-853 (1998).
Nathan et al., "The Effect of Intensive Treatment of Diabetes on the Development and Progression of Long-Term Complications in Insulin-Dependent Diabetes Mellitus", The New England Journal of Medicine, vol. 329, No. 14, pp. 977-986 (1993).
G. Van Den Berghe et al., "Intensive Insulin Therapy in Critically Ill Patients", The New England Journal of Medicine, vol. 345, No. 19, pp. 1359-1367 (2001).
M.P. Weinstein et al., Clinical Importance of Identifying Coagulase-Negative Staphylococci Isolated from Blood Cultures: Evaluation of MicroScan Rapid and Dried Overnight Gram-Positive Panels versus a Conventional Reference Method:, Journal of Clin. Microbiol. vol. 36, No. 7, pp. 2089-2092 (1998).

(Continued)

*Primary Examiner* — Marcela M Cordero Garcia
(74) *Attorney, Agent, or Firm* — Teresa Chen

(57) ABSTRACT

Use of medicament for life saving treatment of critically ill patients and method of treatment. The medicament comprises a GLP-1 compound which effectively controls the blood glucose level.

28 Claims, No Drawings

OTHER PUBLICATIONS

Fantus, George et al., Biochemistry, 1989, vol. 28, pp. 8864-8871.
Swarup Ghanshyam et al., Biochem Biophys, 1982, vol. 107, Part 3, pp. 1104-1109.
Lindner et al., N. Eng. J. Med., 1996, vol. 334, pp. 1448-1460.
J. Rudinger. In: Peptide Hormones, JA Parsons, Ed. (1976) 1-7.
SIGMA. Designing Custom Peptides (Accessed Dec. 16 2004), 2 pages.
H.J.C. Berendsen, "A Glimpse of the Holy Grail?", Science (1998)282, pp. 642-643.
D. Voet and J.G. Voet., Biochemistry, $2^{nd}$ Edition, (1995), pp. 235-241.
D.E. Smilek et al., Proc. Natl. Acad. Sci. USA (1991) 88, pp. 9633-9637.
Analogue: definition at www.answers.com/analog. Accessed online Dec. 6, 2005, one page.
Derivative: definition at www.answers.com/analog. Accessed online Dec. 6, 2004, one page.
R.R. Wolfe et al., "Glucose Metabolism in Man: Responses to Intravenous Glucose Infusion", Metabolism, vol. 28, No. 3, pp. 210-220 (1979).
R.R. Wolfe et al., "Effect of Severe Burn Injury on Substrates Cycling by Glucose and Fatty Acids", The New England Journal of Medicine, vol. 317, No. 17, pp. 403-408 (1987).
R.E. Shangraw et al., "Differentiation Between Septic and Postburn Insulin Resistance", Metabolism, vol. 38, No. 10, pp. 983-989 (1989).
Sturis et al., Long-Acting GLP-1 derivative NN2211, EASD, Sep. 2000.
Knudsen et al., Potent Derivatives of Glucagon-like Peptide-1 with Pharmacokinetic Properties Suitable for Once Daily Administration, J. Med. Chem., Apr. 2000, vol. 43, pp. 1664-1669.
R. Fietsman et al., "Complications of Coronary Artery Surgery in Diabetic Patients", The American Surgeon, vol. 57, pp. 551-557 (1991).
P.A. O'Neill et al., "Stress Hormone and Blood Glucose Response Following Acute Stroke in the Elderly", Stroke, vol. 22, pp. 42-847 (1991).
J.F. Scott et al., "Glucose Potassium Insulin Infusions in the Treatment of Acute Stroke Patients with Mild to Moderate Hyperglycemia", The Glucose Insulin in Stroke Trial (GIST), Stroke, vol. 30, pp. 793-799 (1999).
K. Malmberg et al., "Glycometabolic State at Admission: Important Risk Marker of Mortality in Conventionally Treated Patients with Diabetes Mellitus and Acute Myocardial Infarction", Circulation, vol. 99, pp. 2626-2632 (1999).
K. Malmberg et al., "Prospective randomized study of intensive insulin treatment on long term survival after acute myocardial infarction in patients with diabetes mellitus", BMJ, vol. 314:1512, pp. 1-12 (1997).
K. Malmberg et al., "Randomized Trial of Insulin-Glucose Infusion followed by Subcutaneous Insulin Treatment in Diabetic Patients with Acute Myocardial Infarction (GIGAMI Study): Effects on Mortality at One Year", J. Am. Coll. Cardio. vol. 26, pp. 57-65 (1995).
G. Van Den Berghe et al., "Reactivation of Pituitary Hormone Release and Metabolic Improvement by Infusion of Growth Hormone-Releasing Peptide and Thyrotropin-Releasing Hormone in Patients with Protracted Critical Illness", The Journal of Clinical Endocrinology & Metabolism, vol. 84, No. 4, pp. 1311-1323 (1999).
G. Van Den Berghe et al., "A Paradoxical Gender Disassociation within the Growth Hormone/Insulin-like Growth Factor I Axis during Protracted Critical Illness", The Journal of Clinical Endocrinology & Metabolism, vol. 85, No. 1, pp. 183-192 (2000).
A. Ortiz et al., "Expression of Apopotsis-Regulatory Genes in Renal Proximal Tubular Epithelial Cells Exposed to High Ambient Glucose and in Diabetic Kidneys", Journal of Investigative Medicine, vol. 45, No. 2, pp. 50-56 (1997).
Gerard Said et al., "Severe Early-Onset Polyneuropathy in Insulin-Dependent Diabetes Mellitus", The New England Journal of Medicine, vol. 326, No. 19, pp. 1257-1263 (2992).
Wiley W. Souba, "Nutritional Support", The New England Journal of Medicine, vol. 336, No. 1, pp. 41-48 (1997).

W.A. Knaus et al., "APACHE II: A Severity of Disease Classification System", Critical Care Medicine, vol. 13, No. 10, pp. 818-829 (1985).
D.R. Miranda et al., Simplified Therapeutic Intervention Scoring System: The TISS-28 Items-Results from a Multicenter Study, Crit. Care Med., vol. 24, No. 1, pp. 64-73 (1996).
A.R. Keene et al., "Therapeutic Intervention Scoring System: Update 983", Crit. Care Med., vol. 11, No. 1, pp. 1-3 (1983).
W.A. Knaus, "Measuring the Glasgow Coma Scale in the Intensive Care Unit: Potentials and Pitfalls", Intensive Care World, p. 102.
M.P. Weinstein et al., "Clinical Importance of Identifying Coagulase-Negative Staphylocci Isolated from Blood Cultures: Evaluation of the Microbiology, Epidemiology, and Outcome of Bacteremia and Fungemia in Adults", Clinical Infectious Diseases, vol. 24, pp. 584-602 (1997).
C.S. Levetan et al., "Hospital Management of Diabetes", Acute Complications of Diabetes, vol. 29, No. 4, pp. 745-770 (2000).
J. Takala et al., "Increased Mortality Associated with Growth Hormone Treatment in Critically Ill Adults", The New England Journal of Medicine, vol. 341, No. 11, pp. 785-792 (1999).
K.G.M.M. Albert et al., Definition, Diagnosis and Classification of Diabetes Mellitus and its Complications Part 1: Diagnosis and Classification of Diabetes Mellitus Provisional Report of a WHO Consultation, Diabetic Medicine, vol. 15 pp. 539-543 (1998).
S.E. Capes et al., "Stress Hyperglycemia and Increased Risk of Death After Myocardial Infarction in Patients with and without Diabetes: A Systematic Overview", The Lancet, vol. 355, pp. 773-778 (2000).
G.R. Bernard et al., "Efficacy and Safety of Recombinant Human Activated Protein C for Severe Sepsis", The New England Journal of Medicine, vol. 344, No. 10, pp. 699-709 (2001).
E.J. Rayfield et al., "Infection and Diabetes: The Case for Glucose Control", The American Journal of Medicine, vol. 72, pp. 439-450 (1982).
S.E. Geerlings et al., "Immune Dysfunction in Patients with Diabetes Mellitus (DM)", FEMS Immunology and Medical Microbiology, vol. 26.
A.J. Rassias et al., Insulin Infusion Improves Neutrophil Function in Diabetic Cardia Surgery Patients, Anesth. Analg, vol. 88, pp. 1011-1016 (1999).
M.R. Losser et al., "Glucose Modulates Hemodynamic, Metabolic, and Inflammatory Responses to Lipopolysaccharide in Rabbits", The American Physiological Society, pp. 1566-1574.
Australian and New Zealand Intensive Care Society (ANZIC) Clinical Trials Groups, "Low-Dose Dopamine in Patients with Early Renal Dysfunction: A Placebo-Controlled Randomized Trial", The Lancet, vol. 356, pp. 2139-2143 (2000).
A. Lassnigg et al., "Lack of Renoprotective Effects of Dopamine and Furosemide During Cardiac Surgery", J. Am. Soc. Nephrol, vol. 11, pp. 97-104 (2000).
J. Lewis et al., "Atrial Natriuretic Factor in Oliguric Acute Renal Failure", American Journal of Kidney Diseases, vol. 36, No. 4, pp. 767-774 (2000).
Correspondence "Acute Renal Failure", The New England Journal of Medicine, vol. 335, No. 17, pp. 1320-1322 (1996).
R.S. Jones et al., "Insulin's Effect on File Flow and Lipid Excretion During Euglycemia and Hypoglycemia", Digestive Diseases and Sciences, vol. 29, No. 1, pp. 33-39 (1984).
J.J. Garcia-Marin et al., "Diabetes-Induced Cholestasis in the Rat: Possible Role of Hyperglycemia and Hypoinsulinemia", Hepatology, vol. 8, No. 2, pp. 332-340 (1988).
Per Sidenius, "The Axonopathy of Diabetic Neuropathy", Diabetes, vol. 31, pp. 356-363 (1982).
A.A. Ferrando et al., "A Submaximal Dose of Insulin Promotes Net Skeletal Muscle Protein Synthesis in Patients with Severe Burns", Annals of Surgery, vol. 229, No. 1, pp. 11-18 (1999).
T.J. Orchard, "From Diagnosis and Classification to Complications and Therapy", Diabetes Care, vol. 17, No. 4, pp. 326-338 (1994).
G. Hawthorne et al., "Outcome of Pregnancy in Diabetic Women in Northeast England and in Norway, 1994-1997", BMJ, vol. 321, pp. 730-731 (2000).
English Language Abstract for RU2036659, published Jun. 9, 1995.

\* cited by examiner

SEQUENCE LISTING

<160> NUMBER OF SEQ ID NOS: 2

<210> SEQ ID NO 1
<211> LENGTH: 31

```
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (31)..(31)
<223> OTHER INFORMATION: X=P OR Y

<400> SEQUENCE: 1

His Gly Glu Phe Thr Phe Thr Ser Asp Leu Ser Lys Gln Met Glu Glu
1               5                   10                  15

Glu Ala Val Arg Leu Phe Ile Glu Trp Leu Lys Asn Gly Gly Xaa
            20                  25                  30

<210> SEQ ID NO 2
<211> LENGTH: 40
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (2)..(3)
<223> OTHER INFORMATION: X= SD (exendin-3) or GE (exendin-4)

<400> SEQUENCE: 2

His Xaa Xaa Gly Thr Phe Ile Thr Ser Asp Leu Ser Lys Gln Met Glu
1               5                   10                  15

Glu Glu Ala Val Arg Leu Phe Ile Glu Trp Leu Lys Asn Gly Gly Pro
            20                  25                  30

Ser Ser Gly Ala Pro Pro Pro Ser
            35                  40
```

USE OF GLP-1 COMPOUND FOR TREATMENT OF CRITICALLY ILL PATIENTS

CROSS-REFERENCE TO RELATED APPLICATIONS

This application is a continuation of U.S. application Ser. No. 11/451,635 filed Jun. 13, 2006, which is a continuation of U.S. application Ser. No. 10/359,324 filed Feb. 6, 2003 and claims priority under 35 U.S.C. 119 of Danish application No. PA 2002 00184 filed Feb. 7, 2002 and U.S. provisional application No. 60/359,834 filed Feb. 26, 2002, the contents of which are fully incorporated herein by reference.

FIELD OF THE INVENTION

The present invention relates to methods for prevention, treatment and/or cure of critically ill patients. More specifically, the methods and uses of the invention pertains to administration of a GLP-1 compound or a pharmaceutical medicament comprising a GLP-1 compound to critically ill patients. Furthermore, the present invention relates to a method for marketing GLP-1 compounds and to advertising media used for disseminating information.

BACKGROUND OF THE INVENTION

A specific type of polyneuropathy develops in patients that are treated within an intensive care unit (hereinafter also designated ICU) for several days to weeks and this for a variety of primary injuries or illnesses. This polyneuropathy, known as "Critical Illness Polyneuropathy" (hereinafter also designated CIPNP) occurs in about 70% of patients who have the systemic inflammatory response syndrome (SIRS) (Zochodne D W et al. 1987 Polyneuropathy associated with critical illness: a complication of sepsis and multiple organ failure. Brain, 110: 819-842); (Leijten F S S & De Weerdt A W 1994 Critical illness polyneuropathy: a review of the literature, definition and pathophysiology. Clinical Neurology and Neurosurgery, 96: 10-19). However, clinical signs are often absent and it remains an acute problem in many ICUs worldwide. Nonetheless, it is an important clinical entity as it is a frequent cause of difficulty in weaning patients from the ventilator and it leads to problems with rehabilitation after the acute illness has been treated and cured.

When CIPNP is severe enough, it causes limb weakness and reduced tendon reflexes. Sensory impairment follows but is difficult to test in ICU patients. Electrophysiological examination (EMG) is necessary to establish the diagnosis (Bolton C F. 1999 Acute Weakness. In: Oxford Textbook of Critical Care; Eds. Webb A R, Shapiro M J, Singer M, Suter P M; Oxford Medical Publications, Oxford UK; pp. 490-495). This examination will reveal a primary axonal degeneration of first motor and then sensory fibers. Phrenic nerves are often involved. Acute and chronic denervation has been confirmed in muscle biopsies of this condition. If the underlying condition (sepsis or SIRS) can be successfully treated, recovery from and/or prevention of the CIPNP can be expected. This will occur in a matter of weeks in mild cases and in months in more severe cases. In other words, the presence of CIPNP can delay the weaning and rehabilitation for weeks or months.

The pathophysiology of this type of neuropathy remains unknown (Bolton C F 1996 Sepsis and the systemic inflammatory response syndrome: neuromuscular manifestations. Crit Care Med. 24: 1408-1416). It has been speculated to be directly related to sepsis and its mediators. Indeed, cytokines released in sepsis have histamine-like properties which may increase microvascular permeability. The resulting endoneural edema could induce hypoxia, resulting in severe energy deficits and hereby primary axonal degeneration. Alternatively, it has been suggested that cytokines may have a direct cytotoxic effect on the neurons. Contributing factors to disturbed microcirculation are the use of neuromuscular blocking agents and steroids. Moreover, a role for aminoglucosides in inducing toxicity and CIPNP has been suggested. However, there is still no statistical proof for any of these mechanisms in being a true causal factor in the pathogenesis of CIPNP.

Polyneuropathy of critical illness was first described in 1985 by three different investigators, one Canadian, one American, and one French. Until recently there was no effective treatment to prevent or stop Critical Illness Polyneuropathy. Until recently the current standard of practice of care, especially of critically ill patients, was that within the settings of good clinical ICU practice, blood glucose levels are allowed to increase as high as to 250 mg/dL or there above. The reason for this permissive attitude is the thought that high levels of blood glucose are part of the adaptive stress responses, and thus do not require treatment unless extremely elevated (Mizock B A. Am J Med 1995; 98: 75-84). Also, relative hypoglycaemia during stress is thought to be potentially deleterious for the immune system and for healing (Mizock B A. Am J Med 1995; 98: 75-84).

The recent work of G. Van Den Berghe showed that mortality in an ICU could be reduced by strictly controlling the blood glucose level with insulin (WO 01/85256). Although insulin is very effective for treating hyperglycaemia and has widespread therapeutic applications developed over the past 80 years, insulin may also produce hypoglycaemic events when administered in high dosages.

Human GLP-1 is a 37 amino acid residue peptide originating from preproglucagon which is synthesised i.a. in the L-cells in the distal ileum, in the pancreas and in the brain. GLP-1 is an important gut hormone with regulatory function in glucose metabolism and gastro-intestinal secretion and metabolism. Processing of preproglucagon to give GLP-1(7-36)-amide, GLP-1(7-37) and GLP-2 occurs mainly in the L-cells. The fragments GLP-1(7-36)-amide and GLP-1(7-37) are both glucose-dependent insulinotropic agents. In the past decades a number of structural analogs of GLP-1 were isolated from the venom of the Gila monster lizards (*Heloderma suspectum* and *Heloderma horridum*). Exendin-4 is a 39 amino acid residue peptide isolated from the venom of *Heloderma horridum*, and this peptide shares 52% homology with GLP-1. Exendin-4 is a potent GLP-1 receptor agonist which has been shown to stimulate insulin release and ensuing lowering of the blood glucose level when injected into dogs. The group of GLP-1(1-37), exendin-4(1-39), certain fragments thereof, analogs thereof and derivatives thereof, (hereinafter designated GLP-1 compounds) are potent insulinotropic agents. Most importantly the group of GLP-1(1-37), exendin-4(1-39), insulinotropic fragments thereof, insulinotropic analogs thereof and insulinotropic derivatives thereof (hereinafter designated GLP-1 compounds) I are also glucose-dependent in their action, i.e. they normalize hyperglycemia but as blood glucose concentration decreases their activity attenuates so that the risk of hypoglycemic events are eliminated or greatly reduced as compared to the conventional treatment with insulin. This lack of severe side effect from overdosing GLP-1 compounds make them very well suited to the therapeutic application within ICU. The density of intense monitoring and multiple treatments of patients in ICU makes

SUMMARY OF THE INVENTION

This invention is based on the discovery that critical illness in a patient and/or CIPNP can be prevented, treated or cured, at least to a certain extent, by controlling glucose metabolism during said critical illness by applying intensive treatment with a GLP-1 compound.

Blood glucose level is kept below an upper limit which is about 110 mg/dL, about 120 mg/dL or about 130 mg/dL. More specifically, blood glucose level is clamped within a range where the lower limit can be selected to be about 60, about 70 or about 80 mg/dL and the upper limit can be selected to be about 110, about 120 or about 130 mg/dL, more specifically to the normal range (i.e., from about 80 to about 110 mg/dL). The skilled art worker, for example, the physician, will be able to decide exactly which upper and lower limits to use. Alternatively, the range is from about 60 to about 130, preferably, from about 70 to about 120, more preferred, from about 80 to about 110 mg/dL.). The skilled art worker will be able to determine the dosage of GLP-1 compound without risking to induce a hypoglycaemic event because GLP-1 compounds have a glucose-dependent action where insulin release is attenuated at lower blood glucose concentrations.

One object of the present invention is to provide a treatment or cure of a critically ill patient and/or a CIPNP patient and/or a potential CIPNP patient.

Another object of the present invention is to increase the survival rate of critically ill patients and/or CIPNP patients and/or potential CIPNP patients.

Another object of the present invention is to provide a treatment or cure that reduces the time where a critically ill patient and/or a CIPNP patient and/or a potential CIPNP patient is hospitalized.

Another object of the present invention is to prevent that a patient becomes critically ill or develops CIPNP.

Another object of the present invention is to prevent, treat or cure SIRS in a patient.

Another object of the present invention is to prevent or reduce the likelihood of a patient suffering from bacteraemia, septicaemia and/or septic shock during hospitalization.

Another object of the present invention is to prevent or reduce the likelihood that a critically ill patient and/or a CIPNP patient and/or a potential CIPNP patient acquires an infectious disease.

Another object of the present invention is to prevent or reduce the likelihood that a critically ill patient and/or a CIPNP patient and/or a potential CIPNP patient acquires an infectious disease with a mortal outcome.

Another object of the present invention is to prevent or reduce the likelihood that a critically ill patient and/or a CIPNP patient and/or a potential CIPNP patient dies due to an infection.

Another object of the present invention is to reduce the rate of infection with mortal outcome in critically ill patients and/or CIPNP patients and/or potential CIPNP patients in an ICU.

Another object of the present invention is to provide a treatment or cure that reduces mortality, duration of hospitalization, frequency of bacteraemia, frequency of septicaemia, frequency of septic shock, need for dialysis, and/or need for ventilatory support in a critically ill patient and/or a CIPNP patient and/or a potential CIPNP patient.

Another object of the present invention is to treat a critically ill patient and/or a CIPNP patient and/or a potential CIPNP patient, so that said patient is no longer in need of vital organ system support.

Another object of the present invention is to treat a critically ill patient and/or a CIPNP patient and/or a potential CIPNP patient, so that it is considered sufficient for said patient to receive at least about two third of the caloric need through the normal enteral route.

Another object of the present invention is to reduce the risk or likelihood from multiple organ failure in a critically ill patient and/or a CIPNP patient and/or a potential CIPNP patient.

Another object of the present invention is to reduce the risk or likelihood from multiple organ failure with a proven septic focus on post-mortem examination in a critically ill patient and/or a CIPNP patient and/or a potential CIPNP patient.

Another object of the present invention is to reduce mortality, for example, in-hospital mortality, in a critically ill patient and/or in a CIPNP patient and/or a potential CIPNP patient.

Another object of the present invention is to reduce morbidity, for example, in-hospital morbidity, in a critically ill patient and/or in a CIPNP patient and/or a potential CIPNP patient.

Another object of the present invention is to reduce the use of mechanical ventilatory support to a critically ill patient and/or to a CIPNP patient and/or a potential CIPNP patient.

Another object of the present invention is to reduce the likelihood of renal replacement therapy and/or renal failure in a critically ill patient and/or a CIPNP patient and/or a potential CIPNP patient.

Another object of the present invention is to reduce the likelihood of disturbed kidney function parameters in a critically ill patient and/or a CIPNP patient and/or a potential CIPNP patient.

Another object of the present invention is to reduce the likelihood of hyper-bilirubinemia in a critically ill patient and/or a CIPNP patient and/or a potential CIPNP patient.

Another object of the present invention is to reduce the likelihood for blood stream infections in a critically ill patient and/or a CIPNP patient and/or a potential CIPNP patient.

Another object of the present invention is to reduce the likelihood of disturbance in markers of inflammations and/or inflammatory responses in a critically ill patient, and/or a CIPNP patient and/or a potential CIPNP patient.

Another object of the present invention is to reduce the use of antibiotics in a critically ill patient and/or a CIPNP patient and/or a potential CIPNP patient.

Another object of the present invention is to reduce the likelihood of a critically ill patient and/or a CIPNP patient and/or a potential CIPNP patient having repetitive positive EMGs.

Another object of the present invention is to reduce the amount of red cell transfusion to a critically ill patient and/or a CIPNP patient and/or a potential CIPNP patient.

Another object of the present invention is to prevent or reduce the amount of ultimately futile intensive care to a critically ill patient and/or a CIPNP patient and/or a potential CIPNP patient.

Another object of the present invention is to protect a critically ill patient and/or a CIPNP patient and/or a potential CIPNP patient from cholestasis.

Another object of the present invention is to reduce the need for invasive treatment in a critically ill patient and/or a CIPNP patient and/or a potential CIPNP patient.

In accordance with the present invention GLP-1 compounds are provided for use in the prevention, treatment or cure of a critically ill patient and/or a CIPNP patient and/or a potential CIPNP patient.

This invention demonstrates that controlling blood glucose levels within the above range, for example, within normal limits (about 80 to about 110 mg/dL) in a critically ill patient or in a chronic ill patient can be used to significantly reduce the incidence of critical illness in a patient and/or CIPNP and to lengthen the time free of critical illness in a patient and/or CIPNP in a patient that do develop this problem.

The invention provides a use of a GLP-1 compound for preventing or reducing the likelihood of a patient suffering from bacteraemia, septicaemia and/or septic shock during hospitalization.

The invention also provides a use of a GLP-1 compound for preventing or reducing the likelihood that a critically ill patient and/or a CIPNP patient and/or a potentially CIPNP patient acquires an infectious disease.

The invention also provides a use of a GLP-1 compound for preventing or reducing the likelihood that a critically ill patient and/or a CIPNP patient and/or a potentially CIPNP patient dies due to an infection.

The invention also provides a use of a GLP-1 compound for reducing the rate of infection with mortal outcome in critically ill patients and/or CIPNP patients and/or potentially CIPNP patients.

According to the present invention, blood glucose levels are controlled by treatment with GLP-1 compounds. However after this invention, it will be clear for the man skilled in the art that also other agonists of the GLP-1 receptor, prodrugs thereof and their physiologically tolerated salts can be used to obtain the same outcome.

DEFINITIONS

The term "systemic inflammatory response syndrome (SIRS)", as used herein refers to the uncontrolled disease process which ensues an initial insult and which gives rise to a multisystem disturbance secondary to inflammatory mediators released during shock.

The term "sepsis", as used herein refers to "SIRS", as described above, which is particularly caused by an infectious insult leading to the initial shock phase.

The term "mediators of sepsis", as used herein refers to factors released by inflammatory cells, such as TNFs, interleukins, bradykinins etc.

The term "insulin receptor type tyrosine kinase", as used herein refers to a post-receptor signal transduction pathway involved in the insulin signaling.

The term "endoneural edema", as used herein refers to swelling of the neuronal cells.

The term "phrenic nerves", as used herein refers to the left and right nervus phrenicus, innervating the diaphragm.

The term "GLP-1 compound", as used herein refers to GLP-1(1-37), exendin-4(1-39), insulinotropic fragments thereof, insulinotropic analogs thereof and insulinotropic derivatives thereof. Insulinotropic fragments of GLP-1(1-37) are insulinotropic peptides for which the entire sequence can be found in the sequence of GLP-1(1-37) and where at least one terminal amino acid has been deleted. Examples of insulinotropic fragments of GLP-1(1-37) are GLP-1(7-37) wherein the amino acid residues in positions 1-6 of GLP-1(1-37) have been deleted, and GLP-1(7-36) where the amino acid residues in position 1-6 and 37 of GLP-1(1-37) have been deleted. Examples of insulinotropic fragments of exendin-4(1-39) are exendin-4(1-38) and exendin-4(1-31). The insulinotropic property of a compound may be determined by in vivo or in vitro assays well known in the art. For instance, the compound may be administered to an animal and monitoring the insulin concentration over time. Insulinotropic analogs of GLP-1(1-37) and exendin-4(1-39) refer to the respective molecules wherein one or more of the amino acids residues have been exchanged with other amino acid residues and/or from which one or more amino acid residues have been deleted and/or from which one or more amino acid residues have been added with the proviso that said analogue either is insulinotropic or is a prodrug of an insulinotropic compound. Examples of insulinotropic analogs of GLP-1(1-37) are e.g. $Met^8$-GLP-1(7-37) wherein the alanine in position 8 has been replaced by methionine and the amino acid residues in position 1 to 6 have been deleted, and $Arg^{34}$-GLP-1(7-37) wherein the valine in position 34 has been replaced with arginine and the amino acid residues in position 1 to 6 have been deleted, and a fusion protein between GLP-1(7-37) and human serum albumin. Examples of insulinotropic analogs of exendin-4(1-39) is $Ser^2Asp^3$-exendin-4(1-39) wherein the amino acid residues in position 2 and 3 have been replaced with serine and aspartic acid, respectively (this particular analog also being known in the art as exendin-3), and a fusion protein between exendin-4(1-39) and human serum albumin. Insulinotropic derivatives of GLP-1(1-37), exendin-4(1-39) and analogs thereof are what the person skilled in the art considers to be derivatives of these peptides, i.e. having at least one substituent which is not present in the parent peptide molecule with the proviso that said derivative either is insulinotropic or is a prodrug of an insulinotropic compound. Examples of substituents are amides, carbohydrates, alkyl groups and lipophilic substituents. Examples of insulinotropic derivatives of GLP-1(1-37), exendin-4(1-39) and analogs thereof are GLP-1(7-36)-amide, $Arg^{34}$, $Lys^{26}(N^\epsilon$-($\gamma$-Glu($N^\alpha$-hexadecanoyl)))-GLP-1(7-37) and $Tyr^{31}$-exendin-4(1-31)-amide. Further examples of GLP-1(1-37), exendin-4(1-39), insulinotropic fragments thereof, insulinotropic analogs thereof and insulinotropic derivatives thereof are described in WO 98/08871, WO 99/43706, U.S. Pat. No. 5,424,286 and WO 00/09666.

The term "stable GLP-1 analog/derivative", as used herein refers to a GLP-1(1-37) analog or derivative thereof which exhibits an in vivo plasma elimination half-life of at least 10 hours in man, as determined by the method described below. Examples of stable derivatives of GLP-1 analogs can be found in WO 98/08871, WO 99/43706 and WO 02/46227. The method for determination of plasma elimination half-life of a compound in man is: The compound is dissolved in an isotonic buffer, pH 7.4, PBS or any other suitable buffer. The dose is injected peripherally, preferably in the abdominal or upper thigh. Blood samples for determination of active compound are taken at frequent intervals, and for a sufficient duration to cover the terminal elimination part (e.g. Pre-dose, 1, 2, 3, 4, 5, 6, 7, 8, 10, 12, 24 (day 2), 36 (day 2), 48 (day 3), 60 (day 3), 72 (day 4) and 84 (day 4) hours post dose). Determination of the concentration of active compound is performed as described in Wilken et al., Diabetologia 43(51): A143, 2000. Derived pharmacokinetic parameteres are calculated from the concentration-time data for each individual subject by use of non-compartmental methods, using the commercially available software WinNonlin Version 2.1 (Pharsight, Cary, N.C., USA). The terminal elimination rate constant is estimated by log-linear regression on the terminal log-linear part of the concentration-time curve, and used for calculating the elimination half-life.

The term "stable exendin-4 analog/derivative", as used herein refers to a exendin-4(1-39) analog or derivative thereof which exhibits an in vivo plasma elimination half-life of at least 10 hours in man, as determined by the method described above. Typical examples of stable exendin-4 analog/derivatives are exendin-4 compounds chemically modified by acylation, PEGylation and fused to serum albumin or fragments thereof.

The term "blood glucose regulator", as used herein refers to any compound which is able to regulate the blood glucose level. Examples of blood glucose regulators are insulin, insulin derivatives, insulin analogues, compounds that stimulate signal transduction mediated by an insulin receptor type tyrosine kinase in a cell, certain protein-tyrosine phosphatases (PTP's), other Type II antidiabetica, and other biologically active substances having insulin releasing action.

The term "insulin", as used herein refers to insulin from any species such as human insulin, porcine insulin, bovine insulin and salts thereof such as zinc salts and protamin salts.

The term "insulin analogues", as used herein refers to insulin wherein one or more of the amino acid residues have been exchanged with another amino acid residue and/or from which one or more amino acid residue has been deleted and/or from which one or more amino acid residue has been added with the proviso that said insulin analogue has a sufficient insulin activity to lower the blood glucose level. Using results from the so-called free fat cell assay, any skilled art worker, for example, a physician, knows when and which dosages to administer of the insulin analogue. Examples of insulin analogues are described in the following patents and equivalents thereto: U.S. Pat. No. 5,618,913, EP 254,516, EP 280,534, U.S. Pat. No. 5,750,497, and U.S. Pat. No. 6,011,007. Examples of specific insulin analogues are insulin aspart (i.e., $Asp^{B28}$ human insulin), insulin lispro (i.e., $Lys^{B28}$, $Pro^{B29}$ human insulin), and insulin glargine (i.e., $Gly^{A21}$, $Arg^{B31}$, $Arg^{B32}$ human insulin).

The term "derivatives of insulin", as used herein are what a skilled art worker generally considers derivatives, for example, insulin having one or more substituents not present in the parent insulin molecule. Also included in "derivatives of insulin" are derivatives of insulin analogs. Examples of such compounds are described in the following patents and equivalents thereto: U.S. Pat. No. 5,750,497, and U.S. Pat. No. 6,011,007. An example of a derivative of insulin is insulin detemir (i.e., des-$Thr^{B30}$ human insulin γ $Lys^{B29}$ tetradecanoyl).

The term "non-diabetic patient", as used herein refers to a patient who has not been diagnosed as having diabetes.

In its broadest sense, the term a "critically ill patient" (herein designated CIP), as used herein refers to a patient who has sustained or are at risk of sustaining acutely life-threatening single or multiple organ system failure due to disease or injury, a patient who is being operated and where complications supervene, and a patient who has been operated in a vital organ within the last week or has been subject to major surgery within the last week. In a more restricted sense, the term a "critically ill patient", as used herein refers to a patient who has sustained or are at risk of sustaining acutely life-threatening single or multiple organ system failure due to disease or injury, or a patient who is being operated and where complications supervene. In an even more restricted sense, the term a "critically ill patient", as used herein refers to a patient who has sustained or are at risk of sustaining acutely life-threatening single or multiple organ system failure due to disease or injury. Similarly, these definitions apply to similar expressions such as "critical illness in a patient" and a "patient is critically ill".

The term "Intensive Care Unit" (herein designated ICU), as used herein refers to the part of a hospital where critically ill patients are treated. Of course, this might vary from country to country and even from hospital to hospital and said part of the hospital may not necessary, officially, bear the name "Intensive Care Unit" or a translation or derivation thereof. Of course, the term "Intensive Care Unit" also covers a nursing home, a clinic, for example, a private clinic, or the like if the same or similar activities are performed there.

The term "Criticall illness polyneuropathy" (herein designated CIPNP), as used herein refers to the specific type of polyneuropathy that develops in patients treated within an ICU for several days to weeks and this for a variety of primary injuries or illnesses The term "effective dosage", as used herein refers to a dosage which is sufficient in order for the treatment of the patient to be effective.

The term "administration of a GLP-1 compound in combination with a second compound", as used herein refers to the administration of the two compounds in overlapping time periods, i.e. the patient is treated with the GLP-1 compound at a time where said patient is also treated with the second compound or has been treated with the second compound until 24 hours prior to the start of administration of the GLP-1 compound. Hence "administration of a GLP-1 compound in combination with a second compound" is taking place unless the administration of the second compound is stopped at least 24 hours before the start of administration of the GLP-1 compound, irrespective of whether the two compounds are administered as separate pharmaceutical compositions.

The term "medicament", as used herein refers to a pharmaceutical composition suitable for administration of the pharmaceutically active compound to a patient.

The term "GLP-1 agonist", as used herein refers to a molecule, preferably GLP-1 or an analogue or a derivative thereof, or exendin or an analogue or a derivative thereof, or a non-peptidyl compound, which interacts with the GLP-1 receptor and induces the physiogyical and pharmacological characteristics of the GLP-1 receptor. A GLP-1 agonist binds to the GLP-1 receptor with an affinity constant $K_D$, below 1 μM, preferably below 100 nM. Methods for identifying GLP-1 agonists are described in WO 93/19175 (Novo Nordisk A/S). The term "GLP-1 agonist" is also intended to comprise active metabolites and prodrugs thereof, such as active metabolites and prodrugs of GLP-1 or an analogue or a derivative thereof, or exendin or an analogue or a derivative thereof, or a non-peptidyl compound. A "metabolite" is an active derivative of a GLP-1 agonist produced when the GLP-1 agonist is metabolized. A "prodrug" is a compound which is either metabolized to a GLP-1 agonist or is metabolized to the same metabolite(s) as a GLP-1 agonist.

DETAILED DESCRIPTION OF THE INVENTION

Usually the treatment of a critical ill patent requires prolonged minute-to-minute therapy and/or observation, usually and preferably in an intensive care unit (ICU) or a special hospital unit, for example a post operative ward or the like, which is capable of providing a high level of intensive therapy in terms of quality and immediacy.

Examples of a critically ill patient is a patient in need of cardiac surgery, cerebral surgery, thoracic surgery, abdominal surgery, vascular surgery, or transplantation, or a patient suffering from neurological diseases, cerebral trauma, respiratory insufficiency, abdominal peritonitis, multiple trauma, severe burns, or CIPNP.

The glucose metabolism of a clinical ill patient may be controlled by clamping the blood glucose level within the ranges mentioned in connection with the present invention.

The skilled art worker, for example, a physician, may do this using a GLP-1 compound. The skilled art worker is able to find the pharmaceutically effective amount of the GLP-1 compound used and to determine how often it is to be administered (depending on the patients weight, gender, disease condition etc.).

Conveniently, the blood glucose level is kept within the ranges mentioned in connection with the present invention for as long a period of time as the patient is critically ill. Hence, as a general rule, the blood glucose level is kept within the ranges mentioned in connection with the present invention as long as the patient is critically ill. Consequently, the blood glucose level is usually kept within the ranges mentioned in connection with the present invention for a period of time of more than about 8 hours, preferably more than about 24 hours, even more preferred more than about 2 days, especially more than about 4 days, and even more than about 7 days. In certain cases, it may even be preferred that the blood glucose level is kept within the ranges mentioned in connection with the present invention after the patient (previously) considered as being critically ill has been transferred from the Intensive Care Unit to another part of the hospital or even after said patient has left the hospital.

A critical ill patient, optionally entering an ICU, may be fed continuously, on admission with mainly intravenous glucose (for example, about 200 g to about 300 g per 24 hours) and from the next day onward with a standardised feeding schedule aiming for a caloric content up to between about 10 and about 40, preferably between about 20 and about 30, non-protein Calories/kg/24 hours and a balanced composition (for example, between about 0.05 and about 0.4, preferably between about 0.13 and about 0.26, g nitrogen/kg/24 hours and between about 20% and about 40% of non-protein Calories as lipids) of either total parenteral, combined parenteral/enteral or full enteral feeding, the latter mode attempted as early as possible. Other concomitant ICU therapy can be left to the discretion of attending physicians.

Alternatively, the following procedure can be used or it is possible to use a combination or variant of these procedures, as the physician considers advantageous for the patient: A critical ill patient may be fed, on the admission day, using, for example, a 20% glucose infusion and from day 2 onward by using a standardised feeding schedule consisting of normal caloric intake (for example, about 25-35 Calories/kgBW/24 h) and balanced composition (for example, about 20%-40% of the non-protein Calories as lipids and about 1-2 g/kgBW/24 h protein) of either total parenteral, combined parenteral/enteral or full enteral feeding, the route of administration of feeding depending on assessment of feasibility of early enteral feeding by the attending physician. All other treatments, including feeding regimens, were according to standing orders currently applied within the ICU.

In one embodiment the GLP-1 compound is GLP-1(7-37), GLP-1(7-36) amide, or an analog thereof or a derivative thereof. Such GLP-1 compounds include, but are not limited to, $Arg^{26}$-GLP-1(7-37); $Arg^{34}$-GLP-1(7-37); $Lys^{36}$-GLP-1(7-37); $Arg^{26,34}Lys^{36}$-GLP-1(7-37); $Arg^{26,34}$-GLP-1(7-37); $Arg^{26,34}Lys^{40}$-GLP-1(7-37); $Arg^{26}Lys^{36}$-GLP-1(7-37); $Arg^{34}Lys^{36}$-GLP-1(7-37); $Val^{8}Arg^{22}$-GLP-1(7-37); $Met^{8}Arg^{22}$-GLP-1(7-37); $Gly^{8}His^{22}$-GLP-1(7-37); $Val^{8}His^{22}$-GLP-1(7-37); $Met^{8}His^{22}$-GLP-1(7-37); $His^{37}$-GLP-1(7-37); $Gly^{8}$-GLP-1(7-37); $Val^{8}$-GLP-1(7-37); $Met^{8}$-GLP-1(7-37); $Gly^{8}Asp^{22}$-GLP-1(7-37); $Val^{8}Asp^{22}$-GLP-1(7-37); $Met^{8}Asp^{22}$-GLP-1(7-37); $Gly^{8}Glu^{22}$-GLP-1(7-37); $Val^{8}Glu^{22}$-GLP-1(7-37); $Met^{8}Glu^{22}$-GLP-1(7-37); $Gly^{8}Lys^{22}$-GLP-1(7-37); $Val^{8}Lys^{22}$-GLP-1(7-37); $Met^{8}Lys^{22}$-GLP-1(7-37); $Gly^{8}Arg^{22}$-GLP-1(7-37); $Val^{8}Lys^{22}His^{37}$-GLP-1(7-37); $Gly^{8}Glu^{22}His^{37}$-GLP-1(7-37); $Val^{8}Glu^{22}His^{37}$-GLP-1(7-37); $Met^{8}Glu^{22}His^{37}$-GLP-1(7-37); $Gly^{8}Lys^{22}$ $His^{37}$-GLP-1(7-37); $Met^{8}Lys^{22}His^{37}$-GLP-1(7-37); $Gly^{8}Arg^{22}His^{37}$-GLP-1(7-37); $Val^{8}Arg^{22}His^{37}$-GLP-1(7-37); $Met^{8}Arg^{22}His^{37}$-GLP-1(7-37); $Gly^{8}His^{22}His^{37}$-GLP-1(7-37); $Val^{8}His^{22}His^{37}$-GLP-1(7-37); $Met^{8}His^{22}His^{37}$-GLP-1(7-37); $Gly^{8}His^{37}$-GLP-1(7-37); $Val^{8}His^{37}$-GLP-1(7-37); $Met^{8}His^{37}$-GLP-1(7-37); $Gly^{8}Asp^{22}$ $His^{37}$-GLP-1(7-37); $Val^{8}Asp^{22}His^{37}$-GLP-1(7-37); $Met^{8}Asp^{22}His^{37}$-GLP-1(7-37); $Arg^{26}$-GLP-1(7-36)-amide; $Arg^{34}$-GLP-1(7-36)-amide; $Lys^{36}$-GLP-1(7-36)-amide; $Arg^{26,34}Lys^{36}$-GLP-1(7-36)-amide; $Arg^{26,34}$-GLP-1(7-36)-amide; $Arg^{26,34}Lys^{40}$-GLP-1(7-36)-amide; $Arg^{26}Lys^{36}$-GLP-1(7-36)-amide; $Arg^{34}Lys^{36}$-GLP-1(7-36)-amide; $Gly^{8}$-GLP-1(7-36)-amide; $Val^{8}$-GLP-1(7-36)-amide; $Met^{8}$-GLP-1(7-36)-amide; $Gly^{8}Asp^{22}$-GLP-1(7-36)-amide; $Gly^{8}Glu^{22}His^{37}$-GLP-1(7-36)-amide; $Val^{8}Asp^{22}$-GLP-1(7-36)-amide; $Met^{8}Asp^{22}$-GLP-1(7-36)-amide; $Gly^{8}Glu^{22}$-GLP-1(7-36)-amide; $Val^{8}Glu^{22}$-GLP-1(7-36)-amide; $Met^{8}Glu^{22}$-GLP-1(7-36)-amide; $Gly^{8}Lys^{22}$-GLP-1(7-36)-amide; $Val^{8}Lys^{22}$-GLP-1(7-36)-amide; $Met^{8}Lys^{22}$-GLP-1(7-36)-amide; $Gly^{8}His^{22}His^{37}$-GLP-1(7-36)-amide; $Gly^{8}Arg^{22}$-GLP-1(7-36)-amide; $Val^{8}Arg^{22}$-GLP-1(7-36)-amide; $Met^{8}Arg^{22}$-GLP-1(7-36)-amide; $Gly^{8}His^{22}$-GLP-1(7-36)-amide; $Val^{8}His^{22}$-GLP-1(7-36)-amide; $Met^{8}His^{22}$-GLP-1(7-36)-amide; $His^{37}$-GLP-1(7-36)-amide; $Val^{8}Arg^{22}His^{37}$-GLP-1(7-36)-amide; $Met^{8}Arg^{22}His^{37}$-GLP-1(7-36)-amide; $Gly^{8}His^{37}$-GLP-1(7-36)-amide; $Val^{8}His^{37}$-GLP-1(7-36)-amide; $Met^{8}His^{37}$-GLP-1(7-36)-amide; $Gly^{8}Asp^{22}$ $His^{37}$-GLP-1(7-36)-amide; $Val^{8}Asp^{22}His^{37}$-GLP-1(7-36)-amide; $Met^{8}Asp^{22}His^{37}$-GLP-1(7-36)-amide; $Val^{8}Glu^{22}His^{37}$-GLP-1(7-36)-amide; $Met^{8}Glu^{22}His^{37}$-GLP-1(7-36)-amide; $Gly^{8}Lys^{22}$ $His^{37}$-GLP-1(7-36)-amide; $Val^{8}Lys^{22}His^{37}$-GLP-1(7-36)-amide; $Met^{8}Lys^{22}His^{37}$-GLP-1(7-36)-amide; $Gly^{8}Arg^{22}His^{37}$-GLP-1(7-36)-amide; $Val^{8}His^{22}His^{37}$-GLP-1(7-36)-amide; $Met^{8}His^{22}His^{37}$-GLP-1(7-36)-amide; and derivatives thereof.

In another embodiment the GLP-1 compound is a fusion protein between GLP-1(7-37), an analogue or a derivative thereof, and human serum albumin or a variant, e.g. fragment, thereof. In another embodiment the GLP-1 compound is a fusion protein between GLP-1(7-37), an analogue or a derivative thereof, and the Fc portion of an immunoglobulin or a variant, e.g. fragment, thereof.

GLP-1 analogues and derivatives which can be used according to the present invention includes those referred to in WO 99/43705 (Novo Nordisk A/S), WO 99/43706 (Novo Nordisk A/S), WO 99/43707 (Novo Nordisk A/S), WO 98/08871 (Novo Nordisk A/S), WO 99/43708 (Novo Nordisk A/S), WO 99/43341 (Novo Nordisk A/S), WO 87/06941 (The General Hospital Corporation), WO 90/11296 (The General Hospital Corporation), WO 91/11457 (Buckley et al.), WO 98/43658 (Eli Lilly & Co.), EP 0708179-A2 (Eli Lilly & Co.), EP 0699686-A2 (Eli Lilly & Co.), WO 01/98331 (Eli Lilly & Co).

In another embodiment of the invention the GLP-1 compound is selected from exendin as well as analogs, derivatives, and fragments thereof, e.g. exendin-3 and exendin-4. Examples of exendins as well as analogs, derivatives, and fragments thereof to be included within the present invention are those disclosed in WO 9746584, U.S. Pat. No. 5,424,286 and WO 01/04156. U.S. Pat. No. 5,424,286 describes a method for stimulating insulin release with an exendin polypeptide. The exendin polypeptides disclosed include HGEGTFTSDLSKQMEEEAVRLFIEWLKNGGX; wherein X=P or Y, and HX1X2GTFITSDLSKQMEEEAVRLFIEWLKNGGPSSG APPPS; wherein X1X2=SD (exendin-3) or GE (exendin-4)). WO 9746584 describes truncated versions of exendin peptide(s). The disclosed peptides increase secretion and biosynthesis of insulin, but reduce those of glucagon.

In another embodiment the GLP-1 compound is a fusion protein between exendin-4(1-39), an analogue or a derivative thereof, and human serum albumin or a variant, e.g. fragment, thereof. In another embodiment the GLP-1 compound is a fusion protein between exendin-4(1-39), an analogue or a derivative thereof, and the Fc portion of an immunoglobulin or a variant, e.g. fragment, thereof. WO 01/04156 describes exendin-4 analogs and derivatives as well as the preparation of these molecules. Likewise, WO 02/46227 describes GLP-1 compounds which are exendin-4 fusion proteins and the preparation of these molecules.

GLP-1 compounds can be produced by appropriate derivatization of an appropriate peptide backbone which has been produced by recombinant DNA technology or by peptide synthesis (e.g. Merrifield-type solid phase synthesis) as known in the art of peptide synthesis and peptide chemistry.

The route of administration of GLP-1 compounds may be any route, which effectively transports the active compound to the appropriate or desired site of action, such as oral, nasal, buccal, pulmonal, transdermal or parenteral.

Medicaments or pharmaceutical compositions containing a GLP-1 compound, such as $Arg^{34}$, $Lys^{26}(N^{\epsilon}$-($\gamma$-Glu($N^{\alpha}$-hexadecanoyl)))-GLP-1(7-37), may be administered parenterally to a critically ill patient and/or a CIPNP patient and/or a potential CIPNP patient. Parenteral administration may be performed by subcutaneous, intramuscular or intravenous injection by means of a syringe, optionally a pen-like syringe. Alternatively, parenteral administration can be performed by means of an infusion pump. A further option is a composition which may be a powder or a liquid for the administration of a GLP-1 compound in the form of a nasal or pulmonal spray. As a still further option, the GLP-1 compound can also be administered transdermally, e.g. from a patch, optionally a iontophoretic patch, or transmucosally, e.g. bucally. The above-mentioned possible ways to administer GLP-1 compounds are not considered as limiting the scope of the invention.

Pharmaceutical compositions containing GLP-1 compounds, such as $Arg^{34}$, $Lys^{26}(N^{\epsilon}$-($\gamma$-Glu($N^{\alpha}$-hexadecanoyl)))-GLP-1(7-37), may be prepared by conventional techniques, e.g. as described in Remington's *Pharmaceutical Sciences*, 1985 or in Remington: *The Science and Practice of Pharmacy*, 19$^{th}$ edition, 1995.

Thus, the injectable compositions of GLP-1 compounds can be prepared using the conventional techniques of the pharmaceutical industry which involves dissolving and mixing the ingredients as appropriate to give the desired end product.

According to one procedure, e.g. $Arg^{34}$, $Lys^{26}(N^{\epsilon}$-($\gamma$-Glu($N^{\alpha}$-hexadecanoyl)))-GLP-1(7-37) is dissolved in an amount of water which is somewhat less than the final volume of the composition to be prepared. An isotonicity agent, a preservative and a buffer are added as required and the pH value of the solution is adjusted—if necessary—using an acid, e.g. hydrochloric acid, or a base, e.g. aqueous sodium hydroxide as needed. Finally, the volume of the solution is adjusted with water to give the desired concentration of the ingredients.

Examples of isotonic agents are sodium chloride, mannitol and glycerol.

Examples of preservatives are phenol, m-cresol, methyl p-hydroxybenzoate and benzyl alcohol.

Examples of suitable buffers are sodium acetate and sodium phosphate.

Further to the above-mentioned components, solutions containing a GLP-1 compound may also contain a surfactant in order to improve the solubility and/or the stability of the peptide.

According to one embodiment of the present invention, the GLP-1 compound is provided in the form of a composition suitable for administration by injection. Such a composition can either be an injectable solution ready for use or it can be an amount of a solid composition, e.g. a lyophilised product, which has to be dissolved in a solvent before it can be injected. The injectable solution preferably contains not less than about 0.1 mg/ml, typically from 0.1 mg/ml to 10 mg/ml, such as from 1 mg/ml to 5 mg/ml of GLP-1 compound.

GLP-1 compounds such as $Arg^{34}$, $Lys^{26}(N^{\epsilon}$-($\gamma$-Glu($N^{\alpha}$-hexadecanoyl)))-GLP-1(7-37) can be used in the treatment of all critically ill patients and/or CIPNP patients and/or potential CIPNP patients. The optimal dose level for any patient (effective amount) will depend on the history and state of that particular patient to be treated. The person skilled in the art, e.g. a physician, will know how to determine the optimal dose level in order to control the blood glucose level within intervals mentioned herein.

Furthermore, the present GLP-1 compounds, preferably $Arg^{34}$, $Lys^{26}(N^{\epsilon}$-($\gamma$-Glu($N^{\alpha}$-hexadecanoyl)))-GLP-1(7-37), may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin.

Also, the present GLP-1 compounds may be administered in combination with a compound selected from human growth hormone, growth hormone releasing compounds, a growth factor such as prolactin or placental lactogen, FVII and other factors in the blood clotting cascade.

The present invention also relates to a method of marketing a GLP-1 compound, said method comprising the dissemination of information about the indications, utilities and benefits of a GLP-1 compound or a pharmaceutical composition comprising a GLP-1 compound, said indications, utilities, benefits and GLP-1 compounds being according to the present invention. Another method of marketing a GLP-1 compound according to the present invention is to support a speaker disseminating information about the indications, utilities and benefits of a GLP-1 compound or a pharmaceutical composition comprising a GLP-1 compound, said indications, utilities, benefits and GLP-1 compounds being according to the present invention. Examples are supporting a speaker at a symposium or congress within the fields of medicine, ICU and/or health care economics.

The present invention also relates to advertising media to disseminate information about the indications, utilities and benefits of a GLP-1 compound or a pharmaceutical composition comprising a GLP-1 compound, said indications, utilities, benefits and GLP-1 compounds being according to the present invention. Examples of advertising media and material and information media and material is a brochure, pamphlet, or packaging material which is used for the customer package such as the outer box, the inner box, or a blister-pack, any printed material/leaflet supplied with the medicament such as a package insert, a patient leaflet, or patient information, a label, a web site, a movie, an advertising movie, a video, a DVD, a CD-ROM and the like. The skilled art worker knows how to manufacture the above advertising media and material and information media and material. An example of a brochure according to the present invention is a brochure in which it is stated (or suggested) that insulin can be used to treat critically ill patients and/or CIPNP patients, for example in an ICU.

An advertising medium according to the present invention can have the following text:

---

- to physicians, especially those working in an Intensive Care Unit:
LIFE SAVING TREATMENT
In order to save life, it is important that the blood glucose level of a critically ill patient is kept within the range from about 80 to about 110 mg/dL. This can be done with no risk of hypoglycaemic event by using NN2211 from Novo Nordisk A/S. More information will be available from www.novonordisk.com.

---

The advertising media according to the present invention are preferably presented or distrubuted to physicians working in an ICU and persons responsible for the budget in an ICU.

According to one aspect, the present invention relates to a use of a GLP-1 compound for the manufacture of a medicament for treatment or cure of a critically ill patient and/or a CIPNP patient and/or a potential CIPNP patient.

According to one embodiment, the present invention relates to the novel uses described herein, wherein the treatment or cure increases the survival rate of critically ill patients and/or CIPNP patients and/or potential CIPNP patients.

According to a further embodiment, the present invention relates to the novel uses described herein, wherein the treatment or cure reduces the time where a critically ill patient and/or a CIPNP patient and/or a potential CIPNP patient is hospitalized.

According to a further embodiment, the present invention relates to the novel uses described herein, wherein the patient is hospitalized in an ICU.

According to a further aspect, the present invention relates to a use of a GLP-1 compound for the manufacture of a medicament for preventing that a patient becomes critically ill or develops CIPNP.

According to a further aspect, the present invention relates to a use of a GLP-1 compound for the manufacture of a medicament for prevention, treatment or cure of SIRS in a patient.

According to a further aspect, the present invention relates to a use of a GLP-1 compound for the manufacture of a medicament for preventing or reducing the likelihood of a patient suffering from bacteraemia, septicaemia and/or septic shock during hospitalization.

According to one embodiment, the present invention relates to the novel uses described herein, where the hospitalization is in an ICU.

According to a further embodiment, the present invention relates to the novel uses described herein, wherein the patient is selected from a critically ill patient, a CIPNP patient, a potential CIPNP patient, a SIRS patient and a potential SIRS patient.

According to a further aspect, the present invention relates to a use of a GLP-1 compound for manufacturing a medicament for preventing or reducing the likelihood that a critically ill patient and/or a CIPNP patient and/or a potential CIPNP patient acquires an infectious disease.

According to one embodiment, the present invention relates to the novel uses described herein, wherein the infectious disease has a mortal outcome.

According to a further aspect, the present invention relates to a use of a GLP-1 compound for manufacturing a medicament for preventing or reducing the likelihood that a critically ill patient and/or a CIPNP patient and/or a potential CIPNP patient dies due to an infection.

According to a further aspect, the present invention relates to a use of a GLP-1 compound for manufacturing a medicament for reducing the rate of infection with mortal outcome in critically ill patients and/or CIPNP patients and/or potential CIPNP patients in an ICU.

According to one embodiment, the present invention relates to the novel uses described herein, wherein the treatment or cure reduces mortality, duration of hospitalization, frequency of bacteraemia, frequency of septicaemia, frequency of septic shock, need for dialysis, and/or need for ventilatory support in said patient.

According to a further aspect, the present invention relates to a use of a GLP-1 compound for the manufacture of a medicament to treat a critically ill patient and/or a CIPNP-patient and/or a potential CIPNP-patient so that the patient is no longer in need of vital organ system support or to treat a critically ill patient and/or a CIPNP-patient and/or a potential CIPNP-patient so that it is considered sufficient for the patient to receive at least about two third of the caloric need through the normal enteral route to reduce the risk or likelihood from multiple organ failure, to reduce the risk or likelihood from multiple organ failure with a proven septic focus on post-mortem examination, to reduce mortality, for example, in-hospital mortality, to reduce the use of mechanical ventilatory support, to reduce the likelihood of renal replacement therapy and/or renal failure, to reduce the likelihood of disturbed kidney function parameters, to reduce the likelihood of hyperbilirubinemia, to reduce the likelihood for blood stream infections, to reduce the likelihood of disturbance in markers of inflammations and/or inflammatory responses, to reduce the use of antibiotics, to reduce the amount of red cell transfusion, or to reduce stress induced hyperglycaemia, or to reduce the likelihood of the critically ill patient and/or the CIPNP-patient and/or the potential CIPNP-patient having repetitive positive EMGs, or to prevent or reduce the amount of ultimately futile intensive care to a critically ill patient and/or a CIPNP-patient and/or a potential CIPNP-patient, or to protect a critically ill patient and/or a CIPNP-patient and/or a potential CIPNP-patient from cholestasis, or to reduce the need for invasive treatment in a critically ill patient and/or a CIPNP-patient and/or a potential CIPNP-patient.

According to one embodiment, the present invention relates to the novel uses described herein, wherein the GLP-1 compound is GLP-1(7-36)-amide, GLP-1(7-37), or an analogue thereof or a derivative thereof.

According to a further embodiment, the present invention relates to the novel uses described herein, wherein the GLP-1 compound is a derivative of GLP-1(7-36)-amide or GLP-1(7-37) which comprises a lipophilic substituent.

According to a further embodiment, the present invention relates to the novel uses described herein, wherein the GLP-1 compound is $Arg^{34}$, $Lys^{26}(N^{\epsilon}-(\gamma-Glu(N^{\alpha}-hexadecanoyl)))$-GLP-1(7-37).

According to a further embodiment, the present invention relates to the novel uses described herein, wherein the GLP-1 compound is selected from the group consisting of $Gly^8$-GLP-1(7-36)-amide, $Gly^8$-GLP-1(7-37), $Val^8$-GLP-1(7-36)-amide, $Val^8$-GLP-1(7-37), $Val^8Asp_{22}$-GLP-1(7-36)-amide, $Val^8Asp^{22}$-GLP-1(7-37) $Val^8Glu^{22}$-GLP-1(7-36)-amide, $Val^8Glu^{22}$-GLP-1(7-37), $Val^8Lys^{22}$-GLP-1(7-36)-amide, $Val^8Lys^{22}$-GLP-1(7-37), $Val^8Arg^{22}$-GLP-1(7-36)-amide, $Val^8Arg^{22}$-GLP-1(7-37), $Val^8His^{22}$-GLP-1(7-36)-amide, $Val^8His^{22}$-GLP-1(7-37), analogues thereof and derivatives thereof.

According to a further embodiment, the present invention relates to the novel uses described herein, wherein the GLP-1 compound is selected from the group consisting of $Arg^{26}$-GLP-1(7-37); $Arg^{34}$-GLP-1(7-37); $Lys^{36}$-GLP-1(7-37); $Arg^{26,34}Lys^{36}$-GLP-1(7-37); $Arg^{26,34}$-GLP-1(7-37); $Arg^{26,34}Lys^{40}$-GLP-1(7-37); $Arg^{26}Lys^{36}$-GLP-1(7-37); $Arg^{34}Lys^{36}$-GLP-1(7-37); $Val^8Arg^{22}$-GLP-1(7-37); $Met^8Arg^{22}$-GLP-1(7-37); $Gly^8His^{22}$-GLP-1(7-37); $Val^8His^{22}$-GLP-1(7-37); $Met^8His^{22}$-GLP-1(7-37); $His^{37}$-GLP-1(7-37); $Gly^8$-GLP-1(7-37); $Val^8$-GLP-1(7-37); $Met^8$-GLP-1(7-37); $Gly^8Asp^{22}$-GLP-1(7-37); $Val^8Asp^{22}$-GLP-1(7-37); $Met^8Asp^{22}$-GLP-1(7-37); $Gly^8Glu^{22}$-GLP-1(7-37); $Val^8Glu^{22}$-GLP-1(7-37); $Met^8Glu^{22}$-GLP-1(7-37); $Gly^8Lys^{22}$-GLP-1(7-37); $Val^8Lys^{22}$-GLP-1(7-37); $Met^8Lys^{22}$-GLP-1(7-37); $Gly^8Arg^{22}$-GLP-1(7-37); $Val^8Lys^{22}His^{37}$-GLP-1(7-37); $Gly^8Glu^{22}His^{37}$-GLP-1(7-37); $Val^8Glu^{22}His^{37}$-GLP-1(7-37); $Met^8Glu^{22}His^{37}$-GLP-1(7-37); $Gly^8Lys^{22}His^{37}$-GLP-1(7-37); $Met^8Lys^{22}His^{37}$-GLP-1(7-37); $Gly^8Arg^{22}His^{37}$-GLP-1(7-37); $Val^8Arg^{22}His^{37}$-GLP-1(7-37); $Met^8Arg^{22}His^{37}$-GLP-1(7-37); $Gly^8His^{22}His^{37}$-GLP-1(7-37); $Val^8His^{22}His^{37}$-GLP-1(7-37); $Met^8His^{22}His^{37}$-GLP-1(7-37); $Gly^8His^{37}$-GLP-1(7-37); $Val^8His^{37}$-GLP-1(7-37); $Met^8His^{37}$-GLP-1(7-37); $Gly^8Asp^{22}His^{37}$-GLP-1(7-37); $Val^8Asp^{22}His^{37}$-GLP-1(7-37); $Met^8Asp^{22}His^{37}$-GLP-1(7-37); $Arg^{26}$-GLP-1(7-36)-amide; $Arg^{34}$-GLP-1(7-36)-amide; $Lys^{36}$-GLP-1(7-36)-amide; $Arg^{26,34}Lys^{36}$-GLP-1(7-36)-amide; $Arg^{26,34}$-GLP-1(7-36)-amide; $Arg^{26,34}Lys^{40}$-GLP-1(7-36)-amide; $Arg^{26}Lys^{36}$-GLP-1(7-36)-amide; $Arg^{34}Lys^{36}$-GLP-1(7-36)-amide; $Gly^8$-GLP-1(7-36)-amide; $Val^8$-GLP-1(7-36)-amide; $Met^8$-GLP-1(7-36)-amide; $Gly^8Asp^{22}$-GLP-1(7-36)-amide; $Gly^8Glu^{22}His^{37}$-GLP-1(7-36)-amide; $Val^8Asp^{22}$-GLP-1(7-36)-amide; $Met^8Asp^{22}$-GLP-1(7-36)-amide; $Gly^8Glu^{22}$-GLP-1(7-36)-amide; $Val^8Glu^{22}$-GLP-1(7-36)-amide; $Met^8Glu^{22}$-GLP-1(7-36)-amide; $Gly^8Lys^{22}$-GLP-1(7-36)-amide; $Val^8Lys^{22}$-GLP-1(7-36)-amide; $Met^8Lys^{22}$-GLP-1(7-36)-amide; $Gly^8His^{22}His^{37}$-GLP-1(7-36)-amide; $Gly^8Arg^{22}$-GLP-1(7-36)-amide; $Val^8Arg^{22}$-GLP-1(7-36)-amide; $Met^8Arg^{22}$-GLP-1(7-36)-amide; $Gly^8His^{22}$-GLP-1(7-36)-amide; $Val^8His^{22}$-GLP-1(7-36)-amide; $Met^8His^{22}$-GLP-1(7-36)-amide; $His^{37}$-GLP-1(7-36)-amide; $Val^8Arg^{22}His^{37}$-GLP-1(7-36)-amide; $Met^8Arg^{22}His^{37}$-GLP-1(7-36)-amide; $Gly^8His^{37}$-GLP-1(7-36)-amide; $Val^8His^{37}$-GLP-1(7-36)-amide; $Met^8His^{37}$-GLP-1(7-36)-amide; $Gly^8Asp^{22}His^{37}$-GLP-1(7-36)-amide; $Val^8Asp^{22}His^{37}$-GLP-1(7-36)-amide; $Met^8Asp^{22}His^{37}$-GLP-1(7-36)-amide; $Val^8Glu^{22}His^{37}$-GLP-1(7-36)-amide; $Met^8Glu^{22}His^{37}$-GLP-1(7-36)-amide; $Gly^8Lys^{22}His^{37}$-GLP-1(7-36)-amide; $Val^8Lys^{22}His^{37}$-GLP-1(7-36)-amide; $Met^8Lys^{22}His^{37}$-GLP-1(7-36)-amide; $Gly^8Arg^{22}His^{37}$-GLP-1(7-36)-amide; $Val^8His^{22}His^{37}$-GLP-1(7-36)-amide; $Met^8His^{22}His^{37}$-GLP-1(7-36)-amide; and derivatives thereof.

According to a further embodiment, the present invention relates to the novel uses described herein, wherein the GLP-1 compound is a stable GLP-1 analog/derivative.

According to a further embodiment, the present invention relates to the novel uses described herein, wherein the GLP-1 compound is exendin-4 or an analogue thereof or a derivative thereof.

According to a further embodiment, the present invention relates to the novel uses described herein, wherein the GLP-1 compound is a stable exendin-4 analog/derivative.

According to a further embodiment, the present invention relates to the novel uses described herein, wherein the GLP-1 compound is to be administered parenterally.

According to a further embodiment, the present invention relates to the novel uses described herein, wherein the GLP-1 compound is administered by injection.

According to a further embodiment, the present invention relates to the novel uses described herein, wherein the GLP-1 compound is administered by infusion or drip.

According to a further embodiment, the present invention relates to the novel uses described herein, wherein the dosage of GLP-1 compound is from about 0.5 µg/kg/day to about 20 µg/kg/day.

According to a further embodiment, the present invention relates to the novel uses described herein, wherein the dosage of GLP-1 compound is from about 0.1 µg/kg/day to about 2 µg/kg/day.

According to a further embodiment, the present invention relates to the novel uses described herein, wherein the GLP-1 compound is used such that the blood glucose level is kept below an upper limit which is about 110 mg/dL, about 120 mg/dL or about 130 mg/dL.

According to a further embodiment, the present invention relates to the novel uses described herein, wherein the GLP-1 compound is used such that the blood glucose level is kept within a range where the lower limit is about 60 mg/dL, about 70 mg/dL or about 80 mg/dL and the upper limit is about 110 mg/dL, about 120 mg/dL or about 130 mg/dL, preferably in the range of 80 to about 110 mg/dL.

According to a further embodiment, the present invention relates to the novel uses described herein, wherein the GLP-1 compound is used such that the blood glucose level is kept within a range from about 60 mg/dL to about 130 mg/dL, preferably from about 70 mg/dL to about 120 mg/dL, more preferred from about 80 mg/dL to about 110 mg/dL.

According to a further embodiment, the present invention relates to the novel uses described herein, wherein the blood glucose level is kept within the specified range for a period of more than about 8 hours, preferably for more than about 24 hours, more preferred for more than about 2 days, even more preferred for more than about 4 days, and even more preferred for more than about 7 days.

According to a further embodiment, the present invention relates to the novel uses described herein, wherein a second blood glucose regulator is used.

According to a further embodiment, the present invention relates to the novel uses described herein, wherein the second blood glucose regulator is selected from insulin, insulin analogs, insulin derivatives, insulin secretagogues, insulin compounds that stimulate signal transduction mediated by an insulin receptor type tyrosine kinase in a cell, protein-tyrosine phosphatases and Type II antidiabetica.

According to a further embodiment, the present invention relates to the novel uses described herein, wherein the second blood glucose regulator is selected from insulin, an insulin analog, an insulin derivative, a GLP-1 compound and an orally administered blood glucose regulator.

According to a further embodiment, the present invention relates to the novel uses described herein, wherein treatment, curing or prevention is performed by administering an effective amount of the second blood glucose regulator.

According to a further aspect, the present invention relates to administration of a GLP-1 compound in combination with one or more antihypertensive agents for example (β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin.

According to a further aspect, the present invention relates to administration of a GLP-1 compound in combination with a compound selected from human growth hormone, growth hormone releasing compounds, a growth factor such as prolactin or placental lactogen, FVII and other factors in the blood clotting cascade.

According to a further embodiment, the present invention relates to the novel uses described herein, wherein the patient is a non-diabetic patient.

According to a further embodiment, the present invention relates to the novel uses described herein, wherein the patient is a human.

According to a further embodiment, the present invention relates to the novel uses described herein, wherein the patient is in need of cardiac surgery, cerebral surgery, thoracic surgery, abdominal surgery, vascular surgery, or transplantation, or a patient suffering from neurological diseases, cerebral trauma, respiratory insufficiency, abdominal peritonitis, multiple trauma, severe burns, or CIPNP.

According to a further embodiment, the present invention relates to the novel uses described herein, wherein the patient is fed parenterally.

According to a further embodiment, the present invention relates to the novel uses described herein, wherein the patient receives at least about one third of the caloric need through the normal enteral route, preferably at least about half of the caloric need through the normal enteral route, most preferable at least about two third of the caloric need through the normal enteric route.

According to a further embodiment, the present invention relates to the novel uses described herein, wherein treatment, curing or prevention is performed by administering an effective amount of the GLP-1 compound.

According to a further aspect, the present invention relates to the use of a GLP-1 compound for the treatment or cure of critically ill patients and/or CIPNP patients and/or potential CIPNP patients.

According to one embodiment, the present invention relates to the novel uses described herein, wherein the treatment or cure comprises a pharmaceutically effective composition comprising the GLP-1 compound.

According to a further embodiment, the present invention relates to the novel uses described herein, wherein said use is to attain the clinical benefits mentioned in any one of the preceding claims.

According to a further aspect, the present invention relates to a kit of parts comprising
  a medicament wherein is a GLP-1 compound and
  an insert label stating the use of said medicament for treating critically ill patients within an ICU.

According to a further aspect, the present invention relates to a method of marketing a GLP-1 compound, said method comprising the dissemination of information about the indications, utilities and benefits of a GLP-1 compound or a pharmaceutical composition comprising a GLP-1 compound, said indications, utilities, benefits and GLP-1 compounds being described in the aspects, embodiments and claims of the present invention.

According to one embodiment, the present invention relates to the novel method described herein, wherein the information is disseminated by means of printed material, oral presentation or electromagnetic signals, such as via internet, telephone, television, radio or computer.

According to a further embodiment, the present invention relates to the novel methods described herein, wherein the information is disseminated to physicians and/or persons responsible for health care budgets, preferably to physicians working in an ICU and persons responsible for an ICU budget.

According to a further aspect, the present invention relates to an advertising medium to disseminate information about the indications, utilities and benefits of a GLP-1 compound or a pharmaceutical composition comprising a GLP-1 compound, said indications, utilities, benefits and GLP-1 compounds being described in the uses of the present invention.

According to one embodiment, the present invention relates to the novel advertising media described herein, wherein said advertising media are selected from the group consisting of a brochure, pamphlet, prospectus, videotape, DVD disk and CD disk.

DESCRIPTION OF THE ILLUSTRATIVE EMBODIMENT

The terminology used herein is for the purpose of describing particular embodiments only, and is not intended to limit the scope of the present invention which will be limited only by the appending claims. This invention is not limited to the particular methodology, protocols, delivery forms and reagents described as these may vary.

EXAMPLE 1

Materials and Methods

In a randomized, double-blind, placebo-controlled, cross-over study the effect of NN2211 on beta cell sensitivity to glucose was tested in 10 subjects with type 2 diabetes following a single dose of NN2211 (7.5 µg/kg) or placebo. Using a graded glucose infusion protocol with plasma glucose levels matched over the range of 5 to 12 mmol/L beta cell sensitivity was assessed. Insulin secretion rates (ISR) were estimated by deconvolution of circulating C-peptide concentrations. Findings were compared to responses of 10 healthy, nondiabetic volunteers to the same glucose infusion protocol.

Results

Compared to placebo, a single dose of NN2211 increased insulin and C-peptide levels, increased ISR area under the curve (AUC) ($1130 \pm 150$ vs. $668 \pm 106$ pmol/kg; $p<0.001$), and increased slope of ISR vs. plasma glucose ($1.26 \pm 0.36$ vs. $0.54 \pm 0.18$ pmol*L/(min*mmol*kg); $p<0.014$), to values similar to nondiabetic controls who did not receive the drug (ISR AUC $1206 \pm 99$; slope of ISR vs. plasma glucose $1.44 \pm 0.18$). No hypoglycemic events occurred. Importantly insulin secretion was comparable to the non-diabetic controls at low glucose levels.

Conclusion

A single dose of the long-acting GLP-1 derivative, NN2211, improves beta cell sensitivity to physiological hyperglycemia in type 2 diabetes patients, and confirms that NN2211 provides a glucose-dependent insulin secretion.

EXAMPLE 2

Material and Methods

In a prospective, 12 week, randomised, double-blind, dose-response, placebo controlled and open label glimepiride study in subjects with type 2 diabetes, the glucose lowering effect of NN2211 was tested with the primary endpoint being the effect on HbA1c after 12 weeks treatment (a recognised measure of overall glycaemic control).

Altogether 193 patients were equally randomised to receive one of 5 dose levels of NN2211 (0.045, 0.225, 0.45, 0.60, or 0.75 mg), placebo (s.c. injection), or glimepiride (p.o.) all given once daily. Placebo and NN2211 was double-blind, whereas glimepiride was open-label. The dose of glimepiride was adjusted during the first 4 weeks based on glycaemic control with a treatment target of fasting serum glucose <7 mM, with a dose not exceeding 4 mg/day.

Results

For the primary endpoint of the study $HbA_{1c}$ decreased in all NNC 90-1170 treatment groups, except the one at the lowest dosage. In comparison to the placebo group the decrease was statistically significant for the two highest doses (0.60 and 0.75 mg). After 12 weeks treatment the mean decrease compared to placebo in $HbA_{1c}$ was 0.70 and 0.75 percentage points in the 0.60 and 0.75 mg groups, respectively (p=0.0002 and p<0.0001, respectively.). Furthermore, mean serum fasting glucose decreased by 2.14 and 1.82 mmol/L after 12 weeks in the 0.60 and 0.75 mg NNC 90-1170 dose groups, p<0.0001 and p=0.0003, respectively, compared with placebo. The effect of glimepiride after 12 weeks treatment a reduction compared to placebo of 0.74% (p=0.0001), and −2.6 mM, on HbA1c and FSG, respectively. These effects were not statistically different from the two highest doses of NN2211.

Furthermore, there were 7% of the subjects that reported any hypoglycaemic episode in the two highest dose groups of NN2211, as opposed to 31% in the glimepiride group.

Conclusion

This study demonstrates that NN2211 improves glyceamic control in patients with type 2 diabetes, and furthermore, the low incidence of any hypoglycaemic event also in comparison to glimepiride (that acts by stimulating insulin secretion), corroborates the glucose dependent insulin secretion of NN2211 described in example 1, and suggests its therapeutic advantage on the side effect profile as compared to exogenous insulin administration that is known to be associated with hypoglycaemia if dosing is not carefully titrated. Furthermore, the once daily dosing regimen of NN2211 would be a therapeutic advantage compared to a carefully titrated insulin administration regimen.

EXAMPLE 3

Serves as an example of a study that could determine the effect of NN2211 in critically ill patients in comparison to intensive insulin treatment.

Methods

Study Population

All mechanically ventilated, adult (age>18 y) patients.

Study Design and Treatment Protocols

At ICU admission, and following informed consent, patients are randomized to either strict control of glycemia below 6.1 mmol/L (110 mg/dL) with continuously infused insulin, the 'intensive insulin schedule' (IIS), or using NN2211 given once daily (1-5 mg).

Baseline Assessment and Data Collection

At baseline, demographic, diagnostic and therapeutic information as well as information necessary to determine severity of illness and utilization of ICU resources are obtained from each patient. These include APACHE-II (Acute Physiology and Chronic Health Evaluation) score with higher values indicating more severe illness and simplified Therapeutic Intervention Scoring System (TISS-28) with higher values indicating a higher number of therapeutic interventions. APACHE II and TISS scores are calculated daily from ICU admission to discharge or death.

Continuous blood samples for glucose, clinical chemistry, hematology and markers of inflammation, blood culture (if appropriate). Furthermore, electromyography (EMG) to screen for Critical Illness Polyneuropathy, and in case of ICU death, a post-mortem examination is performed to confirm the presumed cause of death.

Endpoints

The primary endpoint would be death from all causes during intensive care. Secondary outcome measures are in-hospital mortality, incidence of prolonged intensive care dependency and need for ICU re-admission, need for vital organ system support comprising mechanical ventilatory support, renal replacement therapy (continuous or intermittent hemofiltration or dialysis), inotropic or vasopressor support, incidence of critical illness polyneuropathy, the degree of inflammation, incidence of blood stream infections and use of antibiotics, transfusion requirements and incidence of hyperbilirubinemia. Furthermore, use of intensive care resources should be analysed by cumulative TISS scores. In order to accurately and objectively assess duration of ICU stay, which is often influenced by non-patient related factors such as bed availability on regular wards, patients are defined as 'dischargable from ICU' when they were no longer in need of vital organ system support and received at least ⅔rd of the caloric need through the normal enteral route or earlier when actually sent to a ward.

By using published data on variability of the mortality endpoint, together with an expectation of showing a similar effect as intensive insulin therapy (non-inferiority) a sample size calculation are performed in order to determine the number of subjects needed to be recruited.

The invention claimed is:

1. A method for treating a patient having critical illness polyneuropathy (CIPNP), said method comprising administering to said patient a therapeutically effective amount of a GLP-1 compound, wherein the GLP-1 compound is $Arg^{34}$, $Lys^{26}(N^{\epsilon}\text{-}(\gamma\text{-}Glu(N^{\alpha}\text{-hexadecanoyl})))\text{-}GLP\text{-}1(7\text{-}37)$.

2. The method according to claim 1, wherein the GLP-1 compound is administered parenterally.

3. The method according to claim 1, wherein the GLP-1 compound is administered by injection.

4. The method according to claim 1, wherein the GLP-1 compound is administered by infusion or drip.

5. The method according to claim 1, wherein the GLP-1 compound is administered at a dosage of from about 0.5 µg/kg/day to about 20 µg/kg/day.

6. The method according to claim 1, wherein the GLP-1 compound is administered at a dosage of from about 0.1 µg/kg/day to about 2 µg/kg/day.

7. The method according to claim 1, wherein said administration of the GLP-1 compound results in said patient's blood glucose level being kept below an upper limit of about 110 mg/dL.

8. The method according to claim 1, wherein said administration of the GLP-1 compound results in said patient's blood glucose level being kept below an upper limit which is about 120 mg/dL.

9. The method according to claim 1, wherein said administration of the GLP-1 compound results in said patient's blood glucose level being kept below an upper limit which is about 130 mg/dL.

10. The method according to claim 1, wherein said administration of the GLP-1 compound results in said patient's blood glucose level being kept within a range between about 60 mg/dL and about 130 mg/dL.

11. The method according to claim 1, wherein said administration of the GLP-1 compound results in said patient's blood glucose level being kept within a range between about 70 mg/dL and about 120 mg/dL.

12. The method according to claim 1, wherein said administration of the GLP-1 compound results in said patient's blood glucose level being kept within a range between about 80 mg/dL and about 110 mg/dL.

13. The method according to claim 1, wherein said patient is further administered a blood glucose regulator.

14. The method according to claim 13, wherein the blood glucose regulator is selected from the group consisting of insulin, insulin analogs, insulin derivatives, insulin secretagogues, insulin compounds that stimulate signal transduction mediated by an insulin receptor type tyrosine kinase in a cell, protein-tyrosine phosphatases and Type II antidiabetic compounds.

15. The method according to claim 13, wherein the blood glucose regulator is selected from the group consisting of insulin, an insulin analog, an insulin derivative, a second GLP-1 compound and an orally administered blood glucose regulator.

16. The method according to claim 1, wherein the patient is a non-diabetic.

17. The method according to claim 1, wherein the patient is a human.

18. The method according to claim 1, wherein the patient is in need of a surgery selected from the group consisting of cardiac surgery, cerebral surgery, thoracic surgery, abdominal surgery, vascular surgery, and transplantation.

19. The method according to claim 1, wherein the patient is suffering from a condition selected from the group consisting of neurological diseases, cerebral trauma, respiratory insufficiency, abdominal peritonitis, multiple trauma, and severe burns.

20. The method according to claim 1, wherein the patient is fed parenterally.

21. The method according to claim 1, wherein at least about one third of said patient's caloric intake is through the normal enteric route.

22. The method according to claim 1, wherein at least about half of said patient's caloric intake is through the normal enteric route.

23. The method according to claim 1, wherein at least about two third of said patient's caloric intake is through the normal enteric route.

24. The method according to claim 10, wherein said patient's blood glucose level is kept within the specified range for a period of more than about 8 hours.

25. The method according to claim 10, wherein said patient's blood glucose level is kept within the specified range for a period of more than about 24 hours.

26. The method according to claim 10, wherein said patient's blood glucose level is kept within the specified range for a period of more than about 2 days.

27. The method according to claim 10, wherein said patient's blood glucose level is kept within the specified range for a period of more than about 4 days.

28. The method according to claim 10, wherein said patient's blood glucose level is kept within the specified range for a period of more than about 7 days.

* * * * *